United States Patent [19]
Powell et al.

[11] Patent Number: 5,986,145
[45] Date of Patent: Nov. 16, 1999

[54] PURIFICATION OF 3-HYDROXY-PROPANAL

[75] Inventors: Joseph Broun Powell; Paul Richard Weider; Robert Lawrence Blackbourn, all of Houston; Stephen Blake Mullin, Katy, all of Tex.

[73] Assignee: Shell Oil Company, Houston, Tex.

[21] Appl. No.: 09/138,314

[22] Filed: Aug. 21, 1998

Related U.S. Application Data

[60] Provisional application No. 60/056,722, Aug. 22, 1997.
[51] Int. Cl.$^6$ .................................................. C07C 45/00
[52] U.S. Cl. .......................... 568/449; 568/451; 568/454; 568/456; 562/531
[58] Field of Search ..................................... 568/451, 454, 568/483, 496, 862, 867, 881, 576, 449, 456; 560/179; 562/531

[56] References Cited

U.S. PATENT DOCUMENTS

| | | | |
|---|---|---|---|
| 5,786,524 | 7/1998 | Powell et al. ............................ | 568/862 |
| 5,831,121 | 11/1998 | Haas et al. ............................... | 562/531 |

OTHER PUBLICATIONS

Perrin et al, Purification of Laboratory Chemicals, 2nd edition, p. 553, 1980.

*Primary Examiner*—Shailendra Kumar
*Assistant Examiner*—Sreeni Padmanabhan

[57] ABSTRACT

Cobalt or rhodium carbonyl compounds are removed from an aqueous solution of 3-hydroxypropanal by a process comprising the steps of:

(a) contacting the 3-hydroxypropanal solution with oxygen under acidic conditions at a temperature within the range of about 5 to about 45° C. to produce an oxidation product mixture comprising an aqueous solution of 3-hydroxypropanal, one or more water-soluble cobalt or rhodium species, and byproduct carbon monoxide;

(b) removing byproduct carbon monoxide from the oxidation product mixture as it is generated; and (c) passing the oxidation product mixture in contact with an acidic ion exchange resin maintained at a temperature less than about 45° C. and removing at least a portion of the soluble metal compounds from the oxidation product mixture.

Such a process is useful in, for example, the manufacture of 1,3-propanediol from ethylene oxide via an intermediate 3-hydroxypropanal solution containing residual carbon dioxide and insoluble cobalt or rhodium catalyst compounds.

9 Claims, 1 Drawing Sheet

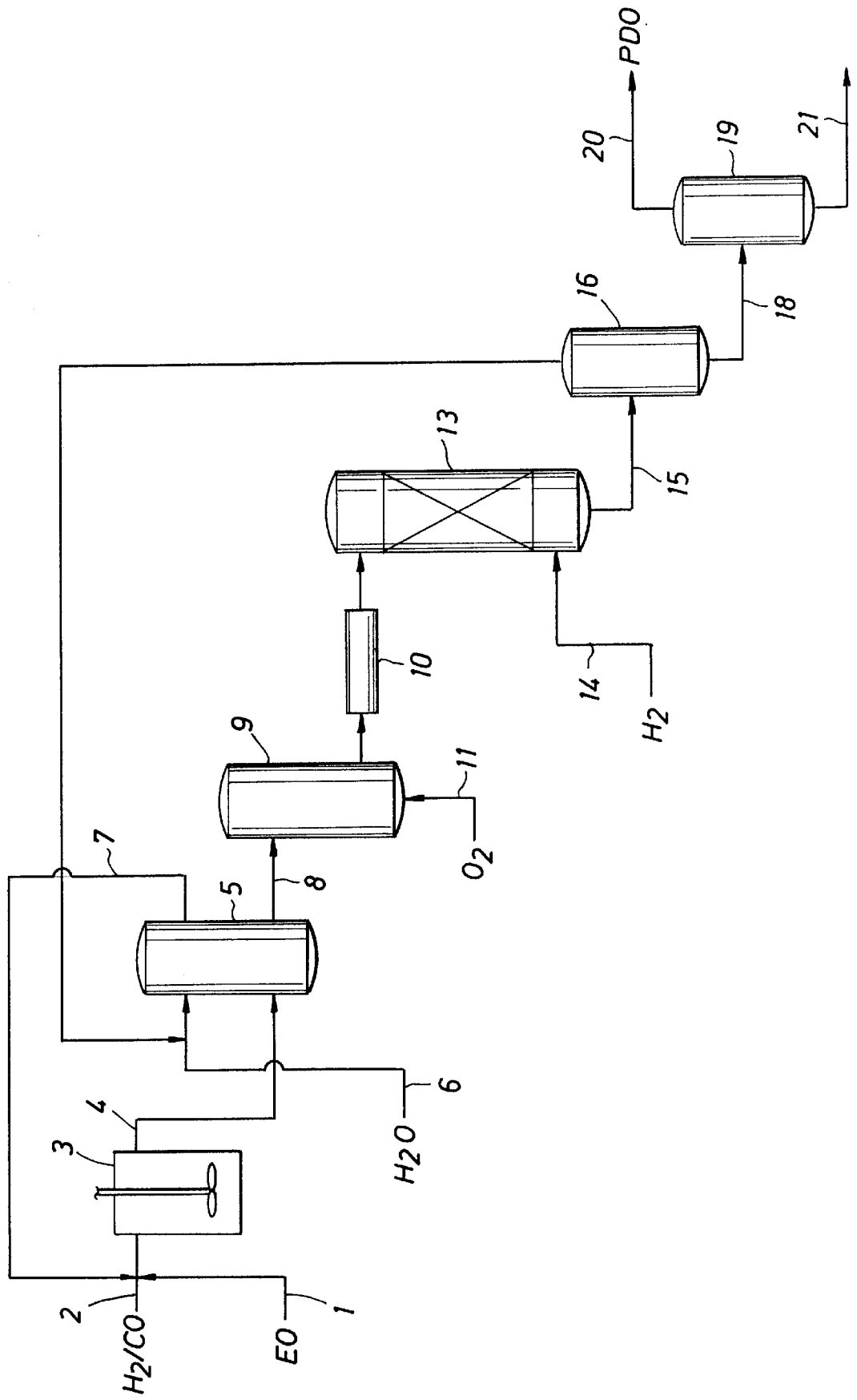

PURIFICATION OF 3-HYDROXY-PROPANAL

This application claims the benefit of U.S. Provisional Application No. 60/056,722 filed Aug. 22, 1997.

BACKGROUND OF THE INVENTION

This invention relates to the selective removal of a metal component from an aqueous stream containing a heat-sensitive component in solution. The invention relates in one aspect to the manufacture of 1,3-propanediol. In one embodiment of this aspect, the invention relates to a cobalt-catalyzed process for preparing 1,3-propanediol in which cobalt is efficiently removed from an intermediate aqueous stream.

1,3-Propanediol is an important industrial chemical which can be prepared in a two-step process in which ethylene oxide is first hydroformylated in organic solution in the presence of a metal catalyst such as a cobalt or rhodium carbonyl, to form 3-hydroxypropanal. The 3-hydroxypropanal intermediate is water extracted under pressure and the cobalt catalyst is recycled to the hydroformylation reaction in the organic phase. The aqueous 3-hydroxypropanal is then hydrogenated to 1,3-propanediol. Ideally, the aqueous 3-hydroxypropanal can be routed directly to the hydrogenation reactor. However, carbon monoxide dissolved in the water is a poison for most heterogeneous hydrogenation catalysts, as is the small amount of metal catalyst which typically leaches into the water phase during extraction of 3-hydroxypropanal. For acceptable product yields, the catalyst must be removed from the aqueous 3-hydroxypropanal solution under conditions which do not degrade the 3-hydroxypropanal.

It is therefore an object of the invention to efficiently remove cobalt and rhodium compounds from an aqueous solution of 3-hydroxypropanal without significant degradation of the 3-hydroxypropanal. In one embodiment, it is a further object of the invention to provide an aqueous 3-hydroxypropanal stream for hydrogenation which is essentially free of carbon monoxide and residual metal compounds.

SUMMARY OF THE INVENTION

According to the invention, cobalt or rhodium carbonyl compounds are removed from an aqueous solution of 3-hydroxypropanal by a process comprising the steps of:

(a) contacting the 3-hydroxypropanal solution with oxygen under acidic conditions at a temperature within the range of about 5 to about 45° C. to produce an oxidation product mixture comprising an aqueous solution of 3-hydroxypropanal, one or more water-soluble cobalt or rhodium species, and byproduct carbon monoxide;

(b) removing byproduct carbon monoxide from the oxidation product mixture as it is generated; and (c) passing the oxidation product mixture in contact with an acidic ion exchange resin maintained at a temperature less than about 45° C. and removing at least a portion of the soluble metal compounds from the oxidation product mixture.

Such a process is useful in, for example, the manufacture of 1,3-propanediol from ethylene oxide via an intermediate 3-hydroxypropanal solution containing residual carbon dioxide and insoluble cobalt or rhodium catalyst compounds.

DETAILED DESCRIPTION OF THE INVENTION

The invention process can be conveniently described by reference to FIG. 1, which illustrates removal of cobalt compounds and carbon monoxide from an aqueous 3-hydroxypropanal solution in a process for preparing 1,3-propanediol by hydroformylation of ethylene oxide to 3-hydroxypropanal followed by hydrogenation of the 3-hydroxypropanal to 1,3-propanediol.

In the illustrated embodiment, separate or combined streams of EO 1, CO and $H_2$ (syngas) 2 are charged to hydroformylation vessel 3, which can be a pressure reaction vessel such as a bubble column or agitated tank, operated batchwise or in a continuous manner. The feed streams are contacted in the presence of a hydroformylation catalyst, generally a metal carbonyl selected from rhodium and cobalt carbonyls. The hydroformylation catalyst will typically be present in the reaction mixture in an amount within the range of about 0.01 to about 1 wt %, preferably about 0.05 to about 0.3 wt %, based on the weight of the hydroformylation reaction mixture. The hydrogen and carbon monoxide will generally be introduced into the reaction vessel in a molar ratio within the range of about 1:2 to about 8:1, preferably about 1:1 to about 6:1.

The hydroformylation reaction is carried out under conditions effective to produce a hydroformylation reaction product mixture containing a major portion of 3-hydroxypropanal and a minor portion of acetaldehyde and 1,3-propanediol, while maintaining the level of 3-hydroxypropanal in the reaction mixture at less than 15 wt %, preferably within the range of about 5 to about 10 wt %. (To provide for solvents having different densities, the desired concentration of 3-hydroxypropanal in the reaction mixture can be expressed in molarity, i.e., less than 1.5M, preferably within the range of about 0.5 to about 1M.). Generally, the cobalt-catalyzed hydroformylation reaction is carried out at elevated temperature less than 100° C., preferably about 60 to about 90° C., most preferably about 75 to about 85° C., with rhodium-catalyzed hydroformylations on the order of about 10° C. higher. The hydroformylation reaction is generally carried out at a pressure within the range of about 100 to about 5000 psig, preferably (for process economics) about 1000 to about 3500 psig, with higher pressures preferred for greater selectivity.

The hydroformylation reaction is carried out in a liquid solvent inert to the reactants. By "inert" is meant that the solvent is not consumed during the course of the reaction. In general, ideal solvents for the hydroformylation process will solubilize carbon monoxide, will be essentially :non-water-miscible and will exhibit low to moderate polarity such that the 3-hydroxypropanal intermediate will be solubilized to the desired concentration of at least about 5 wt % under hydroformylation conditions, while significant solvent will remain as a separate phase upon water extraction. By "essentially non-water-miscible" is meant that the solvent has a solubility in water at 25° C. of less than 25 wt %,, so as to form a separate hydrocarbon-rich phase upon water extraction of 3-hydroxypropanal from the hydroformylation reaction mixture. The preferred class of solvents are alcohols and ethers which can be described by the formula

$$R_2-O-R_1 \qquad (1)$$

in which $R_1$ is hydrogen or $C_{1-20}$ linear, branched, cyclic or aromatic hydrocarbyl or mono- or polyalkylene oxide, and $R_2$ is $C_{1-20}$ linear, branched, cyclic or aromatic hydrocarbyl, alkoxy or mono- or polyalkylene oxide. The most preferred hydroformylation solvents are ethers such as methyl-t-butyl ether, ethyl-t-butyl ether, diethyl ether, phenylisobutyl ether, ethoxyethyl ether, diphenyl ether and diisopropyl ether. Blends of solvents such as tetrahydrofuran/toluene, tetrahydrofuran/heptane and t-butylalcohol/hexane can also be used to achieve the desired solvent properties. The currently preferred solvent, because of the high yields of 3-hydroxypropanal which can be achieved under moderate reaction conditions, is methyl-t-butyl ether.

To further enhance yields under moderate reaction conditions, the hydroformylation reaction mixture will preferably include a catalyst promoter to accelerate the reaction rate. Preferred promoters include lipophilic phosphonium salts and lipophilic amines, which accelerate the rate of hydroformylation without imparting hydrophilicity (water solubility) to the active catalyst. As used herein, "lipophilic" means that the promoter tends to remain in the organic phase after extraction of 3-hydroxypropanal with water. The promoter will generally be present in an amount within the range of about 0.01 to about 1.0 mole per mole of cobalt. The currently preferred lipophilic promoters are tetrabutylphosphonium acetate and dimethyldodecyl amine.

At low concentrations, water serves as a promoter for the formation of the desired carbonyl catalyst species. Optimum water levels for hydroformylation in methyl-t-butyl ether solvent are within the range of about 1 to about 2.5 wt %. Excessive amounts of water, however, reduce (3-hydroxypropanal+1,3-propanediol) selectivity below acceptable levels and may induce formation of a second liquid phase.

Following the hydroformylation reaction, hydroformylation reaction product mixture 4 containing 3-hydroxypropanal, the reaction solvent, 1,3-propanediol, the catalyst, residual syn gas and a minor amount of reaction by-products, is cooled and passed to extraction vessel 5, wherein an aqueous liquid, generally water and optional miscibilizing solvent, are added via 6 for extraction and concentration of the 3-hydroxypropanal for the subsequent hydrogenation step.

Liquid extraction of the 3-hydroxypropanal into the water can be effected by any suitable means, such as mixer-settlers, packed or trayed extraction columns, or rotating disk contactors. The amount of water added to the hydroformylation reaction product mixture will generally be such as to provide a water-mixture ratio within the range of about 1:1 to about 1:20, preferably about 1:5 to about 1:15. Water extraction is preferably carried out at a temperature within the range of about 25 to about 55° C., with lower temperatures preferred. Water extraction under 50 to 200 psig carbon monoxide at 25 to 55° C. maximizes catalyst recovery in the organic phase.

The organic phase containing the reaction solvent and the major portion of the cobalt catalyst can be recycled, with optional purge of heavy ends, from the extraction vessel to hydroformylation reaction via 7. Aqueous extract 8 is passed to hydrogenation zone 13 via flash distillation column 9 and ion exchange resin 10 for removal of residual cobalt or rhodium catalyst. The major portion of residual syn gas is removed from the aqueous solution by flash distillation. It has been found, however, that even minor amounts of carbon monoxide remaining in the solution can interfere with the performance of the hydrogenation catalyst, and the preferred embodiment of the present invention process provides for removal of this residual carbon monoxide as described below prior to passage of the aqueous 3-hydroxypropanal solution to hydrogenation.

The aqueous solution of 3-hydroxypropanal treated by the invention process will typically contain from about 4 to about 60 wt % 3-hydroxypropanal, typically about 20 to about 40 wt % 3-hydroxypropanal, and about 10 to about 400 ppm water-soluble and water-insoluble cobalt or rhodium species such as $Co[Co(CO)_4]_2$, $Co_2(CO)_8$ and $Rh_6(CO)_{16}$.

In the invention process, a weakly acidic, cobalt-containing aqueous solution of 3-hydroxypropanal is contacted with oxygen under conditions effective for oxidation of the insoluble cobalt species to water-soluble cobalt species. The aqueous 3-hydroxypropanal solution can be made sufficiently acidic by addition of an organic or inorganic acid in an amount effective to produce a solution having a pH within the range of about 3 to about 6, preferably about 3 to about 4. Suitable acids include $C_{1-4}$ organic acids. Alternatively, the aqueous acid can be produced as a byproduct of ethylene oxide hydroformylation under conditions favoring the formation of 3-hydroxypropionic acid.

Oxidation can be conveniently carried out by introducing an oxygen-containing gas such as air into the aqueous 3-hydroxypropanal solution. The preferred oxidation technique involves sparging air in an upward direction through a trayed column as the 3-hydroxypropanal solution to be treated flows in a downward direction through the column. The process is carried out at a temperature within the range of about 5 to about 45° C. and at atmospheric pressure. Residence times depend upon other variables but typically range from 1 to about 15 minutes.

Use of a sparging technique for oxidation of insoluble metal species has the added effect of sweeping carbon monoxide from the aqueous solution, particularly if an inert gas such as nitrogen or carbon dioxide is introduced with the oxidation gas to prevent formation of flammable mixtures.

A number of resin types are effective for removing cobalt from an aqueous stream, including alkali metal salts of strong acid resins (e.g., sodium salts of sulfonated polystyrenes); alkali metal salts of weak acid resins; and the acid forms of both strong and weak acid resins. Optimal results are achieved in commercial processes when the resin selected for cobalt or rhodium removal has low potential for 3-hydroxypropanal degradation, can be regenerated in a one-step process, and strongly adsorbs the target metal species. These objectives are best met by the acid form of a strong acid resin, which strongly adsorbs oxidized cobalt species and is readily regenerated in a single step with sulfuric acid. Use of such a resin in a short contact time bed is currently preferred for metal removal. Suitable resins for metal removal are available commercially as IR120, A1200 or A-15 Resins from Rohm & Haas and M-31 resin from Dow Chemical.

In order to minimize degradation of the 3-hydroxypropanal, the temperature of the ion exchange resin should be maintained below about 45° C., and residence times should be kept to a minimum by, for example, use of shortened ionic exchange resin beds. Such beds are designed so as to sharpen the profile of the absorption/ion exchange zone to the point where channeling will not limit bed performance.

It has been found that the ion exchange resin is subject to fouling by residual EO in the aqueous stream. In accordance with one aspect of the invention, contacting the resin with an acid such as 10% sulfuric acid cleans the resin and restores stable ionic exchange performance. The acid is preferably at elevated temperature within the range of about 70 to about 110° C. Treatment times of about 0.5 to about 2 hours are generally sufficient. Recovery of the concentrated cobalt or rhodium from the resin for conversion back to the catalytic carbonyl form is desirable for process economics.

The treated aqueous 3-hydroxypropanal stream 10 is passed to hydrogenation zone 11 and reacted with hydrogen 12 in the presence of a hydrogenation catalyst to produce a hydrogenation product mixture 13 containing 1,3-propanediol. The hydrogenation catalyst is preferably a fixed-bed supported nickel catalyst, such as is available commercially as Calsicat E-475SR and R-3142 from W. R. Grace.

The invention hydrogenation process can be carried out in one stage or in two or more sequential temperature stages. In a preferred embodiment, hydrogenation is carried out as described above at a temperature within the range of about 50 to about 130° C., followed by a second stage carried out at a temperature higher than that of the first stage and within the range of about 70 to about 155° C., and then optionally a third stage at a temperature greater than about 120° C. for reversion of heavy ends to 1,3-propanediol. In such a process, the illustrated hydrogenation zone 11 includes a series of two or more separate reaction vessels.

Residual solvent and extractant water can be recovered by distillation in column 14 and recycled via 15 to the water extraction process via a further distillation (not shown) for separation and purge of light ends. 1,3-Propanediol-containing product stream 16 can be passed to distillation column 17 for recovery of 1,3-propanediol 18 from heavy ends 19.

EXAMPLE 1

Cobalt Poisoning of Nickel Hydrogenation Catalyst

Aqueous solutions of 3-hydroxypropanal intermediate (3-hydroxypropanal) with and without added cobalt were hydrogenated to 1,3-propanediol over a supported nickel catalyst (50% nickel on silica-alumina, 8×14 mesh). Each run used 28 g of fresh catalyst retained in an annular catalyst basket, housed in a 500 mL stirred reactor fitted with a draft-tube impeller to redisperse hydrogen from the headspace to the liquid. Between 320 and 340 g of 3-hydroxypropanal-rich aqueous intermediate were charged to the reactor, which was then pressured to 1000 psi with hydrogen gas. After the reactor was heated to the desired reaction temperature, 1–2 ml samples were periodically withdrawn for analysis of components by gas chromatography.

In Runs 1 and 2, the aqueous 3-hydroxypropanal solution was treated by air oxidation by sparging through a dip tube in the vessels, followed by ion exchange with a strong acid resin (sulfonated polystyrene). Gas chromatography showed that the 3-hydroxypropanal was rapidly hydrogenated to 1,3-propanediol.

In Run 3, the aqueous 3-hydroxypropanal solution was not air sparged or contacted with an ion exchange resin. As a result, 92 ppm of cobalt and residual carbon monoxide remained in the solution. The rate of hydrogenation of 3-hydroxypropanal to 1,3-propanediol was significantly slowed, compared to the rate of Runs 1 and 2.

In Run 4, the aqueous 3-hydroxypropanal solution was first oxidized by air sparging followed by ion exchange treatment to remove residual cobalt. Cobalt was then re-added as cobalt acetate to give an 3-hydroxypropanal solution containing 533 ppm cobalt. The rate of hydrogenation of this solution was also significantly lower than that of the 3-hydroxypropanal solutions which had been treated for cobalt removal.

Runs 1–4 demonstrate that both carbon monoxide and cobalt are poisons for the hydrogenation catalyst, and that oxidative stripping of the 3-hydroxypropanal solution (for removal of carbon monoxide) is not sufficient to prevent hydrogenation catalyst poisoning by residual cobalt.

EXAMPLE 2

Effect of Oxidation on Cobalt Removal with Cation Exchange Resin

For the following runs, aqueous 3-hydroxypropanal solutions were generated in a small-scale continuous pilot plant consisting of two 2 L hydroformylation reactors, in series operated at 80° C. and 1500 psi of 4:1 $H_2$/CO (synthesis gas) through which MTBE solvent was recirculated at 80–100 ml/min and EO reactant was fed to the first reaction stage at 1.8–3.0 ml/min. Soluble dicobaltoctacarbonyl hydroformylation catalyst was supplied at 1200–2000 ppm. Unreacted EO, 3-hydroxypropanal intermediate and catalyst were passed from the second reactor stage and were dispersed into the bottom of a 2-inch diameter extraction column containing 7 sieve plates at 2-inch spacing. Water (45° C.) was fed at 4.5–7 ml/min as the continuous phase extraction solvent. The extraction column was operated at 1200–1400 psi synthesis gas pressure. The aqueous 3-hydroxypropanal stream exiting the bottom of this column typically contained 25–35 wt % 3-hydroxypropanal, 0.2–0.4 wt % EO and 30–200 ppm cobalt.

This aqueous 3-hydroxypropanal stream was routed to a 2-inch diameter by 8-inch tall sight glass, typically operated at the ½-full mark (200 mL), which flashed the liquid by reducing pressure to about atmospheric. A substantial portion of the syn gas dissolved in the 3-hydroxypropanal solution was thus released from the solution. The aqueous solution drawn from the bottom of the vessel on level control contained a small amount of residual syn gas.

For Runs 5 and 6, two samples of this degassed aqueous 3-hydroxypropanal intermediate stream containing 69 ppm cobalt were taken in vials under nitrogen. Each vial contained 1 part by volume of a sulfonated polystyrene strong acid (cation) exchange resin and 3 parts by volume of liquid sample. In Run 6, the vial was sparged with air for 5 minutes, and the other vial remained capped to exclude air. Both vials were rotated for 3 hours to mix, followed by analysis by a calorimetric method (thiocyanate derivatization) to determine cobalt. It was found that 5 ppm cobalt remained in the unoxidized sample, while the cobalt content of the oxidized sampled was reduced to 1 ppm.

EXAMPLE 3

Simultaneous Removal of Syngas and Oxidation of Cobalt

To study continuous oxidation and cobalt removal, a 10-tray, 2-inch diameter glass Oldershaw distillation column was added after the degassing step described in Example 2 above. Aqueous product flowed downward over the column trays at 6–12 mL/min, with maximum 3/16 and typically 3/32-inch tray loading. Oxidizing and stripping gas was added by upflow through the column by blending air and nitrogen in two totameters, delivering 0.2 to 1 SCFH total flow at oxygen concentrations of 2–10 mol %. Dilution of oxygen below its concentration in air was desired to maintain operation outside the flammable region. Depending upon operating history and conditions, a varying number of trays would be inventoried with liquid.

A second column 2 inches in diameter packed with a 6-inch tall or a 24-inch section of ¼-inch perforated stainless steel packing was operated in place of the trayed Oldershaw column for some of the runs, allowing a study of the effect of tray holdup and residence time on oxidation and stripping performance.

A 350 mL bed of strong acid cation exchange resin was positioned downstream from the stripping columns. Incomplete oxidation of cobalt in the feed to this bed could be detected by the appearance of cobalt in the outlet of the ion exchange bed. Samples of the aqueous intermediate feed to the stripper and outlet samples from the ion exchange bed were analyzed for cobalt by the calorimetric method described above. The ion exchange bed was packed with fresh resin prior to the experiments, to insure that cobalt breakthrough from the bed could not be attributed to resin fouling by ethylene oxide.

Results are shown in Table 1. Column C describes the number of trays of the glass column loaded with liquid during the test, or the height of the packed column in inches, for runs conducted in the packed column. Increasing the height of the packed zone, or increasing the number of trays wetted by liquid, increased the area available for contact between liquid and gas phases and increased the time of contact between gas and liquid phases.

Column D notes if free acid was present. A small amount of organic acid is a byproduct of EO hydroformylation. This acid corresponds to at least a 10-fold molar excess relative to the cobalt present, or a 5-fold excess relative to the amount of acid required to oxidize cobalt to $Co(OAc)_2$. If the hydroformylation solvent mixture is recirculated at reaction temperature without EO addition, no acid is formed. A larger fraction of cobalt is extracted into the aqueous stream in the absence of acid. This case corresponds to a notation of "no" acid in column D. Column E shows the diluent gas blended with air to provide stripping capability and to maintain operation outside the flammability window. In most cases nitrogen was used, although Run 19 was conducted with carbon dioxide. Column F gives the total flowrate of the blended stripping gas, in standard cubic feed per hour, while column G gives the mole % oxygen in the blended stripping gas. Column H multiplies these to describe the SCFH flow of oxygen itself. Column I shows the cobalt (ppm) exiting the ion exchange bed. This is the unoxidized cobalt which was not removed by ion exchange. Column J shows the starting amount of cobalt in the aqueous intermediate prior to treatment by oxidation and ion exchange. Column K shows the molar ratio of oxygen to cobalt in the oxidizing stripper. In all cases, an excess of oxygen was supplied.

Run 19 in Table 1 illustrates that, in the absence of stripping and oxidation, very little cobalt is removed by subsequent ion exchange. In Run 20, essentially all the cobalt was removed after stripping and oxidizing the aqueous intermediate in the same column under the described conditions. Runs 9 through 11 show the effect of stripping gas flowrate at fixed oxygen mole percent, for the glass trayed column. Cobalt removal increased as stripping intensity increased. A similar result was observed in the absence of acid for Runs 15–17. Runs 12 and 13 show the effect of mol % oxygen on oxidation efficiency: the ability to oxidize cobalt increases as the concentration (partial pressure) of oxygen in the stripping gas is increased. Comparison of Runs 11 and 14 shows that as the number of trays ("stages") is reduced, oxidation of cobalt is less complete. A similar conclusion is obtained by comparing Runs 20 and 21 in the 24-inch packed column with performance of the 6-inch column in Runs 22–24. In the smaller column, cobalt was incompletely oxidized despite increased oxygen concentrations relative to similar runs in the taller 24-inch packed column.

Runs 12 and 15 show the effect of acid. In the presence of acid, oxidation was complete under conditions where (Run 15) cobalt oxidation was incomplete in the absence of acid, despite a higher oxygen concentration.

Cobalt solids were deposited in the absence of hydroformylation by-product acid. In Run 18, $CO_2$ was used a diluent gas, producing carbonic acid upon absorption into the aqueous intermediate phase. Although this did not appear to increase the extent of oxidation, solids formation was avoided. Addition of $CO_2$ to the glass column was observed to solubilize cobalt deposits formed during operation in the absence of acid with $N_2$ as diluent.

The results summarized in Table 1 suggest that both stripping and oxidation of a cobalt-containing aqueous stream are required to convert the cobalt into a form removable over an ion exchange bed.

TABLE 1

| Run | A Column | B Type | C No. Trays or Packing | D Acid Present? | E Diluent Gas | D Stripping Gas | F Stripping Gas MOL% $O_2$ | H SCFH $O_2$ × 100 | I Co Not Removed By Resin | J Co in Aq. Feed | K Molar Ratio $O_2$/Co |
|---|---|---|---|---|---|---|---|---|---|---|---|
| 9 | GLASS | TRAYED | 7 | YES | $N_2$ | 0.5SCFH | 3 | 1.5 | 0 ppm | 70 ppm | 33 |
| 10 | | TRAYED | 10 | YES | $N_2$ | 0.4 | 2 | 1.2 | 0.5 | 89 | 21 |
| 11 | | TRAYED | 10 | YES | $N_2$ | 0.2 | 3 | 0.6 | 5.6 | 53 | 17 |
| 12 | | TRAYED | 10 | YES | $N_2$ | 0.2 | 5.6 | 1.12 | 0 | 41 | 42 |
| 13 | | TRAYED | 5 | YES | $N_2$ | 0.2 | 5.7 | 1.14 | 0 | 62 | 28 |
| 14 | | TRAYED | 5 | YES | $N_2$ | 0.2 | 3 | 0.6 | 7.5 | 61 | 15 |
| 15 | | TRAYED | 10 | NO | $N_2$ | 0.2 | 10 | 2 | 29 | 205 | 15 |
| 16 | | TRAYED | 10 | NO | $N_2$ | 0.3 | 10 | 3 | 6 | 156 | 29 |
| 17 | | TRAYED | 10 | NO | $N_2$ | 0.4 | 10 | 4 | 0 | 90 | 68 |
| 18 | | TRAYED | 10 | $CO_2$ | $CO_2$ | 0.2 | 10 | 2 | 38 | 246 | 12 |
| 19 | STEEL | PACKED | 24(?) | YES | $N_2$ | 0 | 0 | 0 | 74 | 70 | 0 |
| 20 | | PACKED | 24 | YES | $N_2$ | 0.5 | 2 | 1 | 0 | 70 | 22 |
| 21 | | PACKED | 24 | NO | $N_2$ | 0.5 | 2 | 1 | 0 | 200 | 8 |
| 22 | | PACKED | 6 | YES | $N_2$ | 0.4 | 4.5 | 1.8 | 4 | 50 | 55 |
| 23 | | PACKED | 6 | YES | $N_2$ | 0.2 | 4.5 | 0.9 | 10 | 45 | 30 |
| 24 | | PACKED | 6 | YES | $N_2$ | 0.2 | 5.7 | 1.14 | 4 | 36 | 48 |

EXAMPLE 4

Effect of Acid on Cobalt Oxidation

To examine the effect of acid on cobalt oxidation, a set of experiments was conducted in which the hydroformylation product was extracted in the presence of sodium acetate, resulting in extraction of cobalt primarily as $NaCo(CO)_4$. This allowed a larger concentration of cobalt to be extracted into the aqueous intermediate, such that its concentration now overwhelmed that of the acid formed as a byproduct of EO hydroformylation, and so that oxidation of the cobalt tetracarbonyl anion could be monitored by infrared spectroscopy (1890 $cm^{-1}$). Acetic acid was then added back to adjust the overall equivalents of carboxylic acid species to the equivalents of $Co^{++}$ and $Na^+$, followed by oxidation by air sparging a sample of the final liquid.

Table 2 shows the results of cobalt oxidation of 35° C. with an excess of carboxylic acid. Oxidation continued until essentially complete. Table 3 shows the results of a similar study in which the initial acid concentration was not in excess. The oxidation in this case appeared to stop prior to completion, and it continued only after excess acid was added. These results suggest that organic acid facilitates the oxidation of cobalt.

TABLE 2

| TIME MIN | EXCESS ACID (2Co + Na) | ABSORBANCE 1890 cm−1 | % OXIDIZED | RATE %/HR |
|---|---|---|---|---|
| 0 | 1.6 | 2.09 | 0.00 | N/A |
| 10 | 1.6 | 1.8 | 13.88 | 83 |
| 60 | 1.6 | 0.6 | 71.29 | 69 |
| 120 | 1.6 | 0.07 | 96.65 | 25 |

TABLE 3

| TIME MIN | EXCESS ACID (2Co + Na) | ABSORBANCE 1890 cm−1 | % OXIDIZED | RATE %/HR |
|---|---|---|---|---|
| 0 | 0.6 | 2.09 | 0.00 | N/A |
| 10 | 0.6 | 1.87 | 10.38 | 62 |
| 30 | 0.6 | 1.88 | 10.14 | 0 |
| 60 | 1.2 | 1.27 | 39.29 | 58 |

EXAMPLE 5

Effect of Residual Carbon Monoxide on Cobalt Carbonyl Oxidation

Additional oxidation studies were conducted in a 50 mL stirred reactor fitted with a ZnS (45°) infrared crystal for in-situ monitoring of the cobalt tetracarbonyl anion. The aqueous solution of disproportionated cobalt catalyst for this study was prepared by extracting MTBE solutions of $Co_2(CO)_8$ with water at elevated temperatures at low carbon monoxide partial pressures. This was diluted with distilled water to give a stock solution with a cobalt concentration of 212 ppm by weight free of carboxylic acids. In Run 27, 25 ml of this stock solution was placed into the reactor, which was piped for the introduction of gas via a 1/32" steel tube fitted into the bottom of the reactor. The mixture was heated to 40° C. with stirring and sparging with 100 ml/min nitrogen at ambient pressure. Initial spectra of this mixture revealed cobalt tetracarbonyl anion at 1908 $cm^{-1}$ and a cluster anion at 1979 $cm^{-1}$.

The oxidation was then carried out by switching the sparge gas to 3% oxygen in nitrogen. The extent of reaction can be measured by changes in the infrared spectrum which occur upon oxidation. The spectrum showed an initial increase in cobalt tetracarbonyl anion due to consumption of the cluster anion. The anion was then consumed, forming cobalt (0) carbonyls (both $Co_2(CO)_8$ and $Co(CO)_{12}$ were detected). These carbonyls, were then oxidized and "basic" cobalt carbonate was formed. Under these conditions, complete cobalt oxidation was achieved within 45 minutes.

In Run 28, 25 ml of the stock solution was placed into the 50 ml reactor (with no provisions for gas sparging). The solution was heated to 40° under an atmosphere of nitrogen with vigorous stirring. Oxidation was commenced by pressurizing the vessel to 75 psi with 2% oxygen in nitrogen. To ensure that the oxygen was not depleted from this mixture, the atmosphere was replaced by releasing the pressure and re-pressurizing the reactor with fresh 2% oxygen in nitrogen at 35 and 50 minutes from the start of the reaction. The changes which occurred during this oxidation were the same as in Run 27, in which released carbon monoxide was swept from the reaction mixture, except that the reaction rate was significantly slower. After about one hour, the oxidation was forced by replacing the 2% oxygen mixture with 75 psi of air. Complete oxidation required an additional 25 minutes. The above results demonstrate that free carbon monoxide not stripped from the aqueous intermediate stream, including carbon monoxide bound to cobalt as a ligand, will suppress oxidation of cobalt carbonyl.

EXAMPLE 6

Regeneration of Ionic Exchange Resin

An 83 g bed of A-1200 strong acid gel-form resin (Rohm and Haas) was used to treat 7–12 ml/min of aqueous intermediate extracted from EO hydroformylation product over a one-month period. The aqueous intermediate contained 22–30 wt % 3-hydroxypropanal, 0.1–0.5 wt % residual ethylene oxide, and 40–120 ppm cobalt previously exposed to an oxidation step which included stripping with an $O_2/N_2$ mixture under conditions effective to remove residual carbon monoxide, and oxidize all cobalt to cationic form. After breakthrough of cobalt at the bed outlet, the bed was regenerated by recirculation of 500 ml of 10% sulfuric acid in water at ambient temperature, followed by a 1-hour rinse with deionized water. Adsorption plus regeneration in this manner was considered a "cycle" of operation.

After one month of intermittent operation, the bed was observed to have lost effectiveness in removing cobalt even after regeneration was attempted. A final acid regeneration was attempted for the bed, but no cobalt was detected emerging from the bed with the regeneration acid. The resin had a reddish hue rather than the brown color of fresh resin.

A sample of resin was removed from the bed and heated to 95° C. in 10% sulfuric acid for 3 hours. Some pink color characteristic of cobalt sulfate was observed in the supernatant, suggesting successful regeneration of the resin. Moreover, a brown color characteristic of fresh resin was restored to the resin sample. The treated resin sample was thoroughly washed with deionized water and air dried to a uniform dryness. A portion was soaked with 75 parts 0.1N NaOH overnight, followed by back titration of the supernatant with 0.1N HCl to determine the quantity of $Na^+$ exchanged by the resin. A second portion was dried in a vacuum oven overnight at 90° C. (about 1 psi total pressure), to determine the water content of the resin used in the overnight soak experiment. From these determinations, the equilibrium exchange capacity of the resin was determined as 4.7 meq/g, relative to a theoretical maximum capacity of 4.9–5.1 meq/g for fresh resin.

Resin removed from the on-line bed but not subject to hot acid regeneration was also washed, air dried and equilibrated with 0.1N NaOH to determine capacity. Observed resin capacity was less than 1 meq exchange sites per gram of dry resin. Attempts to regenerate this resin at ambient temperature with 20% sulfuric acid were also made, but essentially no cobalt was released and the resin retained its red color characteristic of fouled resin. Back titration of the resin with 0.1N NaOH revealed essentially no increase in resin capacity (less than 1 meq/g).

This example shows that strong acid cation exchange resin subjected to the aqueous intermediate stream from EO hydroformylation loses its ability to abstract cations such as cobalt despite regeneration with sulfuric acid as commonly practiced at ambient temperature. An elevated temperature (95° C.) was required in the acid regeneration step to restore the resin to near its original capacity. In the absence of hot acid regeneration, the resin eventually lost its ability to remove cobalt.

EXAMPLE 7

A sample of A-15 macroreticular strong acid (cation) exchange resin was exposed to the aqueous intermediate stream from EO hydroformylation for about one month, after which capacity for cobalt removal following ambient temperature regeneration with 10% sulfuric acid had diminished to essentially zero.

A sample of this resin and a sample of fresh resin were analyzed by $^{13}$C NMR. The fouled resin exhibited new chemical shifts at 70 and 60 ppm, indicative of ether linkages —O—$CH_2$—$CH_2$— and terminal —$CH_2OH$, respectively. High temperature (80° C.) regeneration with 10% sulfuric acid essentially removed these peaks from the NMR spectrum. This result suggests fouling of the resin to result from exposure to residual ethylene oxide in the aqueous intermediate stream, as opposed to 3-hydroxypropanal, which would give —O—$CH_2CH_2CH2$— with a corresponding unique chemical shift for the center carbon upon oligomerization over the resin.

EXAMPLE 8

A series of resins were soaked in aqueous solutions of 3-hydroxypropanal doped with varying concentrations of ethylene oxide for 4–20 days at ambient temperature. Following the exposure, the resins were thoroughly washed with deionized water, air dried, and soaked in 0.1N NaOH for determination of ion exchange capacity and assessment of solids content of resin as described above. Results are shown in Table 4.

shows, a lower fraction of capacity remaining (more extensive fouling) for strong acid resin in acid form, relative to weak acid and especially Na-form strong acid.

EXAMPLE 9

Rate of Regeneration of EO-Fouled Resin

The rate of regeneration of resin was examined as a function of temperature for fouled, strong acid resin via soaking samples of the resin in 10% sulfuric acid for varying intervals of time at varying temperatures. Resin samples treated in this manner were removed from the heating bath and separated from acid supernatant in a filter funnel, with thorough washing via deionized water to remove residual supernatant. The samples were then air dried and soaked in 0.1N NaOH for backtitration to determine ion exchange capacity, as described above.

As temperature was increased, the rate of regeneration of active ion exchange capacity by sulfuric acid increased, indicating reversion of fouled resin to be a temperature dependent, kinetic process.

EXAMPLE 10

Continuous studies of acid- and sodium-form strong acid resin were conducted to examine performance under commercial operating conditions. Continuous flow conditions were described in Example 1. For early studies, a 200 ml bed of about 87 dry grams of resin were examined. Later studies employed 12–13 dry grams of resin packed into a 30 ml column constructed from 0.5 inch I.D. Hastelloy C tubing. An annular jacket surrounded the tubing to allow operation at a controlled, above ambient temperature to examine the effect of temperature on the extent of regeneration, as evidenced by the amount of cobalt which could be removed in the next ion exchange cycle.

Results are shown in Table 5. Column F gives the time on line for a given adsorption cycle, G the cumulative time over all cycles. Column H gives the amount of feed treated per

TABLE 4

| Example | Resin Type | Name | EO wt % | Days Soak 25° C. | Liquid/ resin ratio | Capacity after EO soak meq/g | Fresh resin capacity meq/g | Fraction of fresh capacity |
|---|---|---|---|---|---|---|---|---|
| 3A | Strong acid | A15 | 1 | 20 | 25 | 2.42 | 5 | 0.48 |
| 3B | Na-form strong acid | Na-A1200 | 1 | 20 | 25 | 4.19 | 5 | 0.84 |
| 3C | Weak acid | C464 | 1 | 20 | 25 | 3.67 | 6.6 | 0.56 |
| 3D | Strong acid | A15 | 3.2 | 4 | 13 | 2.08 | 5 | 0.42 |
| 3E | Strong acid | A15 | 0.01 | 7 | 25 | 4.9 | 5 | 0.98 |

Comparison of Runs A, D and E shows that the extent of fouling correlates with the concentration of EO present, at essentially fixed 3-hydroxypropanal concentration (25 wt %), with 3-hydroxypropanal present in at least a 4:1 molar excess. This result supports the conclusion derived from $^{13}$C NMR, with fouling and loss of ion exchange capacity resulting from adsorption and reaction of EO on acidic resin sites, and not 3-hydroxypropanal.

Comparison of Runs B and A shows that Na-form resin is less prone to fouling than the strong acid resin. $^{13}$C NMR analysis showed —O—$CH_2CH_2$— or EO-derived fouling for the Na-form strong acid resin and for the weak acid resin, though at lower magnitudes than observed for the strong acid resin. The "fraction of fresh capacity" in Table 4 also unit mass of resin for a given cycle, which "I" gives the cumulative feed treated over all cycles for the given resin type. An adsorption cycle is defined as the time from stream the bed, until cobalt breakthrough occurs at 4 ppmw in the effluent of the bed. Column J gives the wt % cobalt exchanged on the bed at the time of breakthrough, while K gives the ratio of the amount of cobalt removed, relative to the amount which fresh resin would be expected to remove if in equilibrium with the amount of cobalt in the feed (ca. 70 ppmw).

Acid form resin with ambient temperature regeneration by 10% sulfuric acid (series A) exhibited fouling of the resin, such that by the sixth cycle, the resin was no longer effective in removing cobalt. Series B studies (conducted in a smaller bed) demonstrated that sustained removal of cobalt can be achieved via high temperature (95° C.) acid regeneration of the acid-form resin. A steady state configuration was obtained in which cobalt removal capability was stabilized at approximately 30% of the amount which would be expected in the absence of fouling of the resin. (Independent batch studies to determine an adsorption isotherm for cobalt removal over fresh resin were used to determine the equilibrium capacity of fresh (unfouled) resin for a given cobalt concentration in the aqueous intermediate feed).

A third study (series C) examined sodium form strong acid resin. This resin required two regenerants: 10% sulfuric acid, which removed all cobalt and most of the sodium exchanged on the resin, and 4% NaOH, which converted the resin back from acid form to sodium form after acid regen-essentially its unfouled equilibrium capacity, within experimental error, throughout the course of eleven cycles.

A final study (series D) examined acid-form weak acid resin, with the aqueous intermediate stream pH adjusted to 5.5 by caustic addition, to improve resin performance. A larger bed of this resin was required, as a result of ids weaker adsorption (more linear adsorption isotherm). Cobalt breakthrough at 0–2 ppm occurred early, before gradually increasing to a substantial "breakthrough", which was taken as cobalt eluting from the bed at greater than 4 ppm. Ambient temperature regenerations with 10% sulfuric acid were employed for this bed. As evidenced from columns J and K, the bed largely maintained its ability to remove cobalt over 9 cycles.

TABLE 5

Continuous Studies of Cobalt Removal/Regeneration Cycles

| Ex. 5- | Cycle since Fresh Resin | Regen T(°C.) | Resin form | Acid Type | Resin grams (dry) | Hours on-line | Cumulative hours on-line | g-feed/ g-resin treated | Total g-feed/ g-resin treated | wt % cobalt uptake | fraction of equil. capacity |
|---|---|---|---|---|---|---|---|---|---|---|---|
| Strong acid resin with 20° C. regeneration: | | | | | | | | | | | |
| A | 1 | 20 | H+ | strong | 87 | 29 | 29 | 252 | 286 | 2.31 | 0.22 |
| A | 2 | 20 | H+ | strong | 87 | 23 | 52 | 142 | 357 | 0.95 | 0.09 |
| A | 3 | 20 | H+ | strong | 87 | 69 | 121 | 252 | 532 | 1.95 | 0.10 |
| A | 4 | 20 | H+ | strong | 87 | 20 | 141 | 52 | 639 | 0.46 | 0.04 |
| A | 5 | 20 | H+ | strong | 87 | 5 | 146 | 44 | 661 | 0.46 | 0.04 |
| A | 6 | 20 | H+ | strong | 87 | 1 | 147 | 8 | 665 | 0.11 | 0.01 |
| | | | | | | | | | Average: | 0.89 | 0.09 |
| Strong acid resin with 95° C. regeneration: | | | | | | | | | | | |
| B | 1 | 95 | H+ | strong | 12.5 | 10 | 10 | 405 | 505 | 3.12 | 0.30 |
| B | 2 | 95 | H+ | strong | 12.5 | 13 | 23 | 491 | 996 | 4.88 | 0.47 |
| B | 3 | 95 | H+ | strong | 12.5 | 10 | 33 | 471 | 1467 | 3.12 | 0.30 |
| B | 4 | 95 | H+ | strong | 12.5 | 12 | 45 | 432 | 1899 | 2.16 | 0.21 |
| B | 5 | 95 | H+ | strong | 12.5 | 7 | 52 | 250 | 2149 | 2.32 | 0.22 |
| B | 6 | 95 | H+ | strong | 12.5 | 8 | 60 | 281 | 2430 | 2.24 | 0.22 |
| B | 7 | 95 | H+ | strong | 12.5 | 7 | 67 | 240 | 2670 | 2.72 | 0.26 |
| B | 8 | 95 | H+ | strong | 12.5 | 7 | 74 | 296 | 2966 | 5.12 | 0.49 |
| B | 9 | 95 | H+ | strong | 12.5 | 7 | 81 | 300 | 3266 | 3.28 | 0.32 |
| | | | | | | | | | Average: | 3.22 | 0.31 |
| Na-form strong acid resin with 25° C. regeneration: | | | | | | | | | | | |
| C | 1 | 25 | Na+ | strong | 12.1 | 16 | 16 | 832 | 832 | 3.52 | 0.81 |
| C | 2 | 25 | Na+ | strong | 12.1 | 26.5 | 42.5 | 1197 | 2029 | 5.60 | 1.28 |
| C | 3 | 25 | Na+ | strong | 12.1 | 27 | 69.5 | 1359 | 3388 | 6.32 | 1.45 |
| C | 4 | 25 | Na+ | strong | 12.1 | 17 | 86.5 | 837 | 4225 | 3.36 | 0.77 |
| C | 5 | 25 | Na+ | strong | 12.1 | 23 | 109.5 | 1339 | 5564 | 6.88 | 1.57 |
| C | 6 | 25 | Na+ | strong | 12.1 | 14 | 123.5 | 675 | 6239 | 3.87 | 0.89 |
| C | 7 | 25 | Na+ | strong | 12.1 | 23 | 146.5 | 1123 | 7362 | 6.05 | 1.38 |
| C | 8 | 25 | Na+ | strong | 12.1 | 13 | 159.5 | 651 | 8013 | 4.06 | 0.93 |
| C | 9 | 25 | Na+ | strong | 12.1 | 7 | 166.5 | 385 | 8298 | 2.38 | 0.55 |
| C | 10 | 25 | Na+ | strong | 12.1 | 21 | 187.5 | 1032 | 9430 | 5.76 | 1.32 |
| C | 11 | 25 | Na+ | strong | 12.1 | 21 | 208.5 | 1029 | 10459 | 5.62 | 1.28 |
| | | | | | | | | | Average: | 4.86 | 1.11 |
| Na-form weak acid resin with feed buffered to pH 5.5 | | | | | | | | | | | |
| D | 1 | 25 | H+ | weak | 71.2 | 50 | 50 | 422 | 422 | 1.60 | 0.11 |
| D | 2 | 25 | H+ | weak | 71.2 | 28 | 78 | 266 | 688 | 1.12 | 0.07 |
| D | 3 | 25 | H+ | weak | 71.2 | 49 | 127 | 440 | 1128 | 1.83 | 0.12 |
| D | 4 | 25 | H+ | weak | 71.2 | 9 | 136 | 90 | 1218 | 0.35 | 0.02 |
| D | 5 | 25 | H+ | weak | 71.2 | 17 | 153 | 162 | 1380 | 0.29 | 0.02 |
| D | 6 | 25 | H+ | weak | 71.2 | 30 | 183 | 302 | 1682 | 1.42 | 0.09 |
| D | 7 | 25 | H+ | weak | 71.2 | 31 | 214 | 278 | 1960 | 1.26 | 0.08 |
| D | 8 | 25 | H+ | weak | 71.2 | 30 | 244 | 288 | 2248 | 1.29 | 0.09 |
| | | | | | | | | | Average: | 1.15 | 0.08 |

Typical 6.5–10.5 ml/min aqueous flow eration. Regenerant requirements are thus much greater than for regeneration of acid-form resin, and regeneration must be effected in two separate steps. However, the resin retained

What is claimed is:
1. A process for removing a cobalt or rhodium carbonyl compound from an aqueous 3-hydroxypropanal solution, the processing comprising:

(a) contacting the aqueous 3-hydroxypropanal solution with oxygen under acidic conditions at a temperature within the range of about 5 to about 45° C. to produce an oxidation product mixture comprising an aqueous solution of 3-hydroxypropanal, at least one water-soluble cobalt or rhodium species, and byproduct carbon monoxide;

(b) removing byproduct carbon monoxide from the oxidation product mixture as it is generated; and (c) passing the oxidation product mixture in contact with an acidic ion exchange resin maintained at a temperature less than about 45° C. and removing at least a portion of said water-soluble species from the oxidation product mixture on said ion exchange resin.

2. The process of claim 1 in which the pH of the 3-hydroxypropanal solution is within the range of about 3 to about 6.

3. The process of claim 1 in which the aqueous 3-hydroxypropanal solution comprises 3-hydroxypropionic acid.

4. The process of claim 1 in which step (a) is carried out at a temperature within the range of about 5 to about 45° C. and atmospheric pressure.

5. The process of claim 1 in which step (b) is effected by sparging air upwardly through the oxidation product mixture.

6. The process of claim 1 in which the aqueous 3-hydroxypropanal solution contains from about 10 to about 400 ppm cobalt species.

7. The process of claim 6 in which the pH of the aqueous 3-hydroxypropanal is within the range of about 3 to about 4.

8. The process of claim 1 with the additional step that the ion exchange resin is regenerated by contacting it with acid.

9. The process of claim 8 wherein the acid contact is carried out at 70 to 110° C. for 0.5 to 2 hours.

* * * * *